United States Patent [19]

Kemp et al.

[11] Patent Number: 4,797,401

[45] Date of Patent: Jan. 10, 1989

[54] 4-SUBSTITUTED-1-(4-ALKYLSULPHONAMIDOPHENYL)PIPERAZINES AS ANTIARRHYTHMIC AGENTS

[75] Inventors: John E. G. Kemp; Peter E. Cross, both of New York, N.Y.

[73] Assignee: Pfizer Inc., New York, N.Y.

[21] Appl. No.: 73,535

[22] Filed: Jul. 15, 1987

[30] Foreign Application Priority Data

Aug. 9, 1986 [GB] United Kingdom ............... 8619472

[51] Int. Cl.$^4$ .................. A61K 31/495; C07D 241/04
[52] U.S. Cl. .................................. 514/255; 544/392; 544/394
[58] Field of Search ............... 544/392, 394; 514/255

[56] References Cited

U.S. PATENT DOCUMENTS

| | | | |
|---|---|---|---|
| 3,331,845 | 7/1967 | Tomcufcik | 544/392 |
| 3,660,487 | 5/1972 | Larsen et al. | 544/394 |
| 3,758,692 | 9/1973 | Larsen et al. | 544/394 |
| 3,764,602 | 10/1973 | Edenhofer et al. | 544/385 |
| 3,822,266 | 7/1974 | Edenhofer et al. | 544/400 |
| 3,930,004 | 12/1975 | Danilewicz et al. | 514/255 |

FOREIGN PATENT DOCUMENTS

| | | | |
|---|---|---|---|
| 654017 | 10/1964 | Belgium | 544/392 |
| 78756 | 5/1983 | European Pat. Off. | 544/392 |
| 235752 | 9/1987 | European Pat. Off. | |
| 1964423 | 12/1969 | Fed. Rep. of Germany | |
| 42041 | 7/1962 | Luxembourg | |
| 2040279 | 2/1972 | Netherlands | 544/392 |
| 997166 | 7/1965 | United Kingdom | 544/392 |
| 1067817 | 5/1967 | United Kingdom | 544/392 |
| 1361863 | 7/1974 | United Kingdom | 514/255 |

Primary Examiner—Donald G. Daus
Assistant Examiner—Cecilia Shen
Attorney, Agent, or Firm—Peter C. Richardson; Albert E. Frost; Lawrence C. Akers

[57] ABSTRACT

Antiarrhythmic agents of the formula:

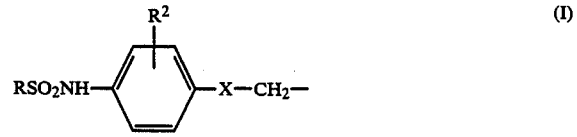

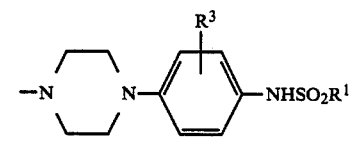

and their pharmaceutically acceptable salts, wherein R and $R^1$, which are the same or different, are $C_1$-$C_4$ alkyl, $C_3$-$C_7$ cycloalkyl, —$CH_2CH_3$, —$CH_2Cl$, —$CF_3$ or —$NH_2$;
$R^2$ and $R^3$, which are the same or different, are H, halo, $CF_3$, $C_1$-$C_4$ alkyl or $C_1$-$C_4$ alkoxy; and
X is —$CH_2$—,

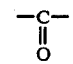

or —CH(OH)—.

4 Claims, No Drawings

4-SUBSTITUTED-1-(4-ALKYLSULPHONAMIDO-PHENYL)PIPERAZINES AS ANTIARRHYTHMIC AGENTS

BACKGROUND OF THE INVENTION

This invention relates to certain sulfonamides which are antiarrhythmic agents.

German Pat. No. 1,964,423 describes a series of aromatic ethers of the general formula

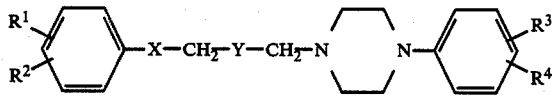

wherein the variables have, inter alia, the values: $R^1$ is amino, lower alkyl sulfonamido; $R^2$ is hydrogen or halogen; each of $R^3$ and $R^4$ is hydrogen, halo, lower alkyl or lower alkoxy; X is O or S; and Y is —CH$_2$—, —CHOH—; and their use as agents for the lowering of blood pressure.

U.S. patent application Ser. No. 10,077, filed Feb. 2, 1987 discloses a series of substituted piperazines of the formula

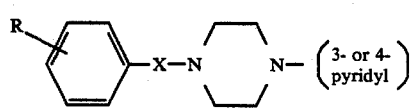

wherein R is NO$_2$, NH$_2$ or NHSO$_2$R$^3$; R$^3$ is, for example, (C$_{1-4}$)alkyl or NR$^1$R$^2$ wherein each of R$^1$ and R$^2$ is independently H or (C$_{1-4}$)alkyl; and X is —(CH$_2$)$_m$—, —CO(CH$_2$)$_n$— or —CH(OH)(CH$_2$)$_n$— wherein m is 1-4 and n is 1-3; and their use as antidisrhythmia agents.

Luxembourg Pat. No. 42041 describes 1,4-disubstituted piperazines of the formula

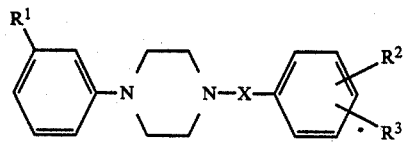

wherein the variables may have, for example, the values: X=—(CH$_2$)$_2$—, —CH$_2$—CO—, or —CH$_2$-CHOH—; R$^1$=H$_2$NSO$_2$—, NO$_2$, or NH$_2$; R$^2$=H, NO$_2$ or NH$_2$; R$^3$=H.

SUMMARY OF THE INVENTION

The compounds of the invention prolong the duration of the action potential in cardiac muscle and conducting tissue, and thereby increase refractoriness to premature stimuli. Thus, they are Class III antiarrhythmic agents according to the classification of Vaughan Williams (Anti-Arrhythmic Action, E. M. Vaughn Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and also produce less neurological side effects. Some of the compounds also have some positive inotropic activity and therefore are particularly beneficial in patients with impaired cardiac pump function.

Thus the invention provides compounds of the formula:

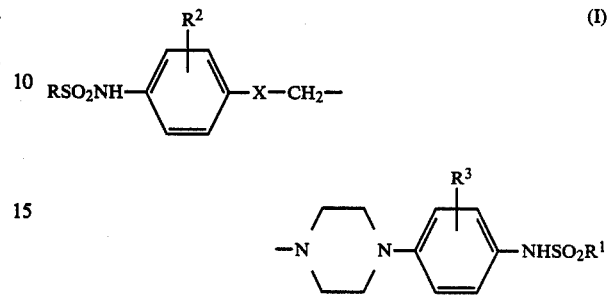

and their pharmaceutically acceptable salts, wherein
R and R$^1$, which are the same or different, are C$_1$-C$_4$ alkyl, C$_3$-C$_7$ cycloalkyl, —CH$_2$CF$_3$, —CH$_2$Cl, —CF$_3$ or —NH$_2$;
R$^2$ and R$^3$, which are the same or different, are H, halo, CF$_3$, C$_1$-C$_4$ alkyl or C$_1$-C$_4$ alkoxy; and
X is —CH$_2$—,

or —CH(OH)—.

"Halo" means F, Cl, Br or I. C$_3$ and C$_4$ alkyl and alkoxy groups can be straight or branched chain.

R and R$^1$ are each preferably C$_1$-C$_4$ alkyl. R and R$^1$ are most preferably CH$_3$. R$^2$ is preferably H and R$^3$ is preferably H, CH$_3$, Cl or F. R$^2$ and R$^3$ are most preferably H. X is preferably —CH$_2$—.

The preferred compound has the formula:

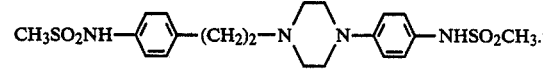

The pharmaceutically acceptable salts of the compounds of the formula (I) include acid addition salts formed from acids which form non-toxic acid addition salts containing pharmaceutically acceptable anions, such as hydrochloride, hydrobromide, hydroiodide, sulphate or bisulphate, phosphsate or hydrogen phosphate, acetate, maleate, fumarate, lactate, tartrate, citrate, gluconate, benzoate, methanesulphonate, besylate and p-toluenesulphonate salts. The compounds also form metal salts, examples of which are the alkaline earth and alkali metal salts, e.g. the sodium and potassium salts. The salts are preparable by conventional techniques.

For assessment of effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli (S$_2$) after every 8th basic stimulus (S$_1$). The S$_1$S$_2$ coupling interval is gradually increased until S$_2$ reproducibly elicits a propagated response. This is defined as the ERP. The concentration of compound required to increase ERP by 25% (ED$_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

The compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the form of tablets containing such excipients as starch of lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditons such as ventricular and supraventricular arrhythmias, including atrial and ventricular fibrillation, it is expected that oral dosages of the compounds of the invention will be in the range from 1 to 75 mg daily, taken in up to 4 divided doses per day, for an average adult patient (70 kg). Dosages for intravenous administration would be expected to be within the range 0.5 to 10 mg per single dose as required. A severe cardiac arrhythmia is preferably treated by the i.v. route in order to effect a rapid conversion to the normal rhythm. Thus, for a typical adult patient individual tablets or capsules might for example contain 1 to 25 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of the formula (I) or pharmaceutically acceptable salt thereof, or of a pharmaceutical composition as defined above.

The invention yet further provides a compound of the formula (I) or a pharmaceutically acceptable salt thereof, for use as a medicament.

The invention also provides the use of a compound of the formula (I), or of a pharmaceutically acceptable salt thereof, for the manufacture of a medicament for the prevention or reduction of cardiac arrhythmias.

Also included within the scope of the invention are the intermediates of the formula:

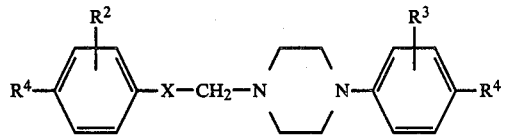

where X, R$^2$ and R$^3$ are as defined for formula (I) and each R$^4$, which is the same, is —NO$_2$ or —NH$_2$. Most preferably, X is —CH$_2$— and R$^2$ and R$^3$ are H.

DETAILED DESCRIPTION OF THE INVENTION

The compounds of the formula (I) can be prepared by the following general routes:

(1) This route, which prepares compounds in which R and R$^1$ are the same, can be illustrated in general terms as follows:

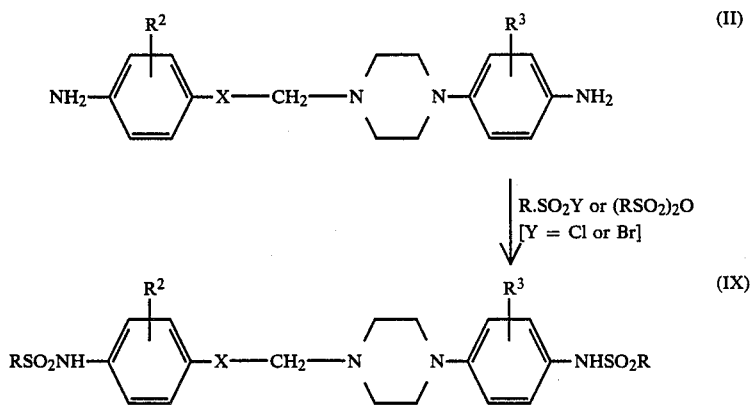

R, R$^2$, R$^3$ and X are as defined for formula (I). To prepare compounds in which R is —NH$_2$, only sulphamyl chloride or bromide can be used in this reaction.

The reaction is typically carried out in a reaction-inert organic solvent, e.g. dichloromethane or dioxan, and preferably in the presence of a base, e.g. pyridine. Preferably, however, the reaction is carried out using pyridine as the solvent. Generally, the reaction proceeds satisfactorily at a temperature of from about 0° to 25° C., i.e. heating is not usually necessary. The reaction is typically carried out at room temperature. The product can be isolated and purified by conventional techniques.

When X is —CH(OH)—, it may be preferable to protect the hydroxy group by a conventional technique prior to acylation, followed by the removal of the protecting group.

The starting materials of the formula (II) are obtainable by conventional techniques as are known to those skilled in the art, and the following Examples illustrate typical syntheses of these compounds. Typical routes are illustrated in general terms as follows:

carried out in an organic solvent such as methanol or dimethylformamide at, say, from room temperature to 150° C. The protecting group is then removed by a conventional technique before the second stage. Acetyl groups are preferably removed by aqueous mineral acid or base, preferably hydrochloric acid at reflux.

(2) Compounds in which R and $R^1$ are both —$NH_2$ are however most conveniently prepared by a modification of route (1) by reacting the intermediate of the formula (II) with sulphamide, typically at 75° to 150°, and preferably under reflux, in a suitable solvent, e.g. dioxan.

(3) This route, which is capable of preparing com-

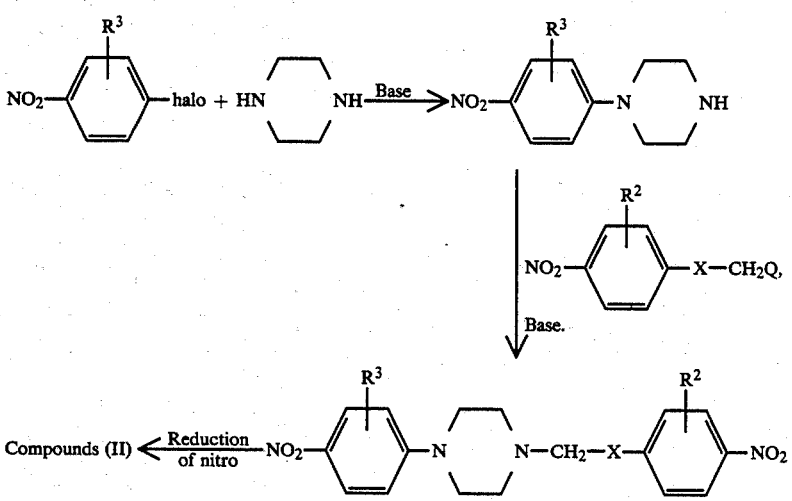

In the above reaction scheme, Q is a leaving group such as halo, $C_1$-$C_4$ alkanesulphonyloxy, phenylsulphonyloxy or p-toluenesulphonyloxy. Q is preferably Br.

The first step in the reaction scheme leading to the compounds (II) is typically carried out in an excess of piperazine, typically about 3 times the weight of the halobenzene derivative, and with a small amount of co-solvent, e.g. dioxan, in an amount of, say, 1 ml. per gram. of said halobenzene derivative, and at the reflux temperature. The product is generally precipitated by diluting the cooled reaction mixture with water.

The second step is typically carried out under reflux in a reaction-inert organic solvent of b.p. 60°–160° C., e.g. acetonitrile, ethanol or butanol, and preferably in the presence of a base such as sodium bicarbonate, potassium carbonate or triethylamine. Sodium iodide can also be added as a catalyst.

The final step can be carried out using conventional reducing agents, e.g. hydrogen in the presence of a palladium or nickel catalyst, tin and hydrochloric acid, stannous chloride or sodium dithionite. If X is a carbonyl group and reduction to —CH(OH)— is not desired, then a reducing agent which selectively reduces nitro should be chosen (e.g. sodium dithionite).

Alternatively, in the first stage of the above scheme it is sometimes preferable to use a mono-protected piperazine, typically 1-acetylpiperazine, in place of piperazine itself [see Examples 3(A) and 4(A).] In such circumstances, the reaction with the halobenzene derivative is typically carried out either using equimolar amounts of the halobenzene and 1-acetylpiperazine in the presence of a base, or using 1 mole of the halobenzene and 2 moles of 1-acetylpiperazine. The reaction is typically pounds in which R and $R^1$ are the same or different, can be illustrated in general terms as follows:

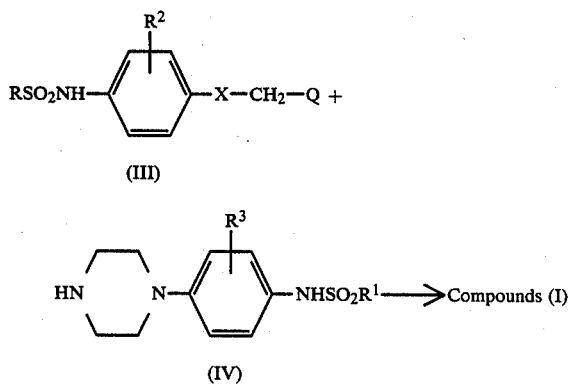

R, $R^1$, $R^2$, $R^3$ and X are as defined for formula (I).

Q is a leaving group such as halo, $C_1$-$C_4$ alkanesulphonyloxy, benzenesulphonyloxy or p-toluenesulphonyloxy.

The preferred leaving groups are methylsulphonyloxy and bromo.

The reaction is typically carried out in an organic solvent such as methanol, ethanol or dichloromethane, at, say, from room temperature to 100° C. It is generally desirable to carry out the reaction in the presence of a base such as triethylamine. Indeed, an acid addition salt of (IV) (e.g. the hydrochloride) can be used as the starting material with excess base being present in the reaction mixture. The product (I) can be isolated and purified by conventional methods.

The starting materials of the formulae (III) and (IV), some of which are known compounds, are obtainable by conventional techniques as are illustrated in the following Examples. Typical technique are illustrated in general terms as follows:

(a)
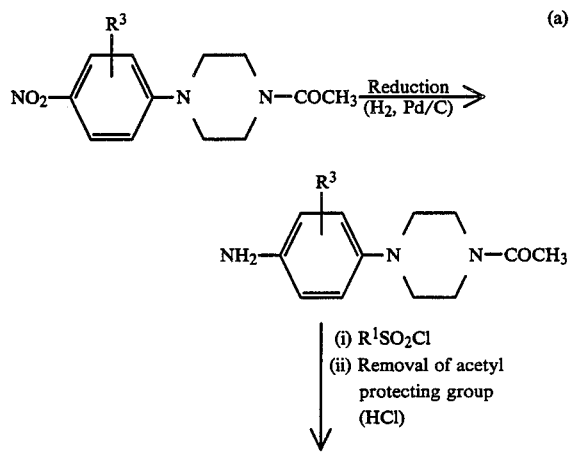

(i) R¹SO₂Cl
(ii) Removal of acetyl protecting group (HCl)

(IV)

(b)
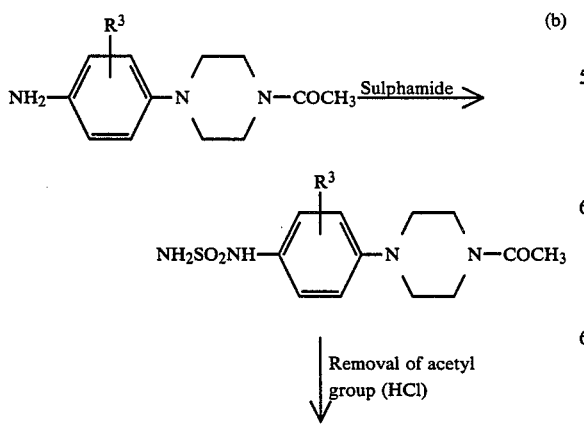

Removal of acetyl group (HCl)

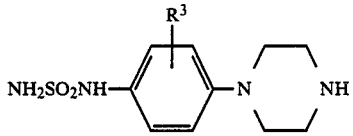

(IVA)

(c)
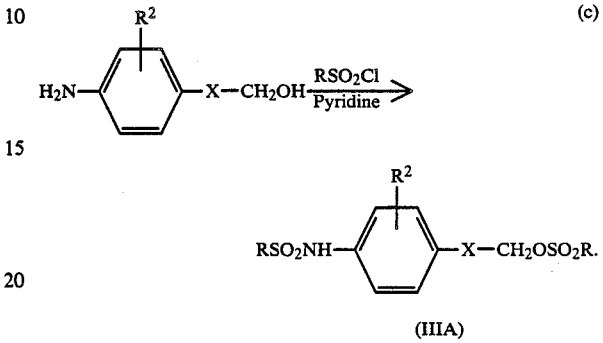

(IIIA)

When R is —NH₂, the following route (d) is preferred, and (d)
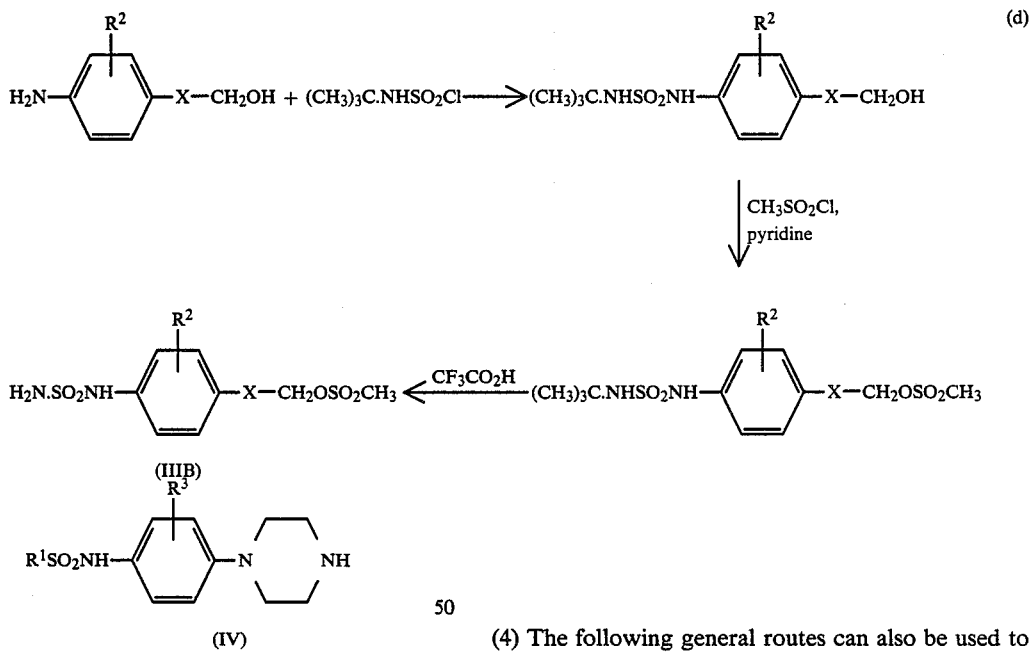

(IIIB)

(4) The following general routes can also be used to prepare compounds in which R and R¹ are the same or different:

(V)

R¹SO₂Y, (R¹SO₂)₂O or sulphamide

Compound (I)

or

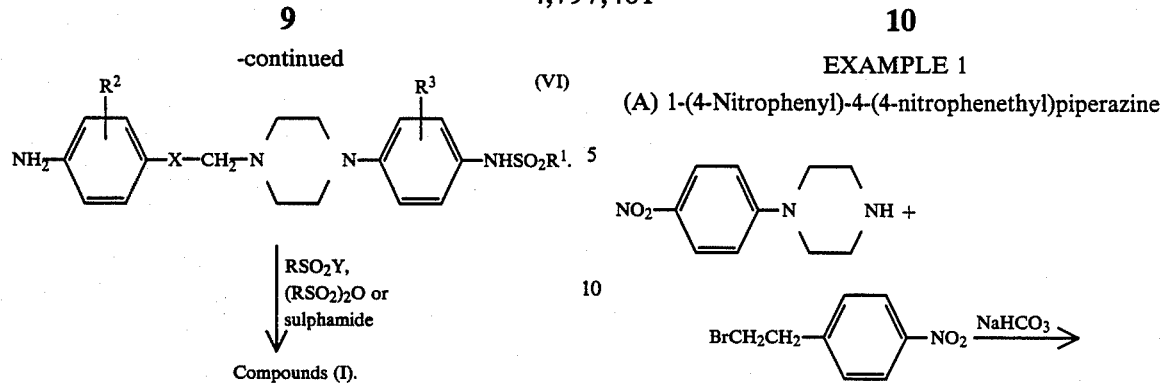

R, $R^1$, $R^2$, $R^3$ and X are as defined for formula (I) except that in the sulphonic anhydride R and $R^1$ are not $NH_2$, and Y is as defined in route (1). The reactions with the sulphonyl or sulphamyl halide and the anhydride can be carried out in a similar manner to that described for route (1), and the reactions with sulphamide, as for route (2) above.

The starting materials (V) and (VI) are again available conventionally, e.g. as follows:

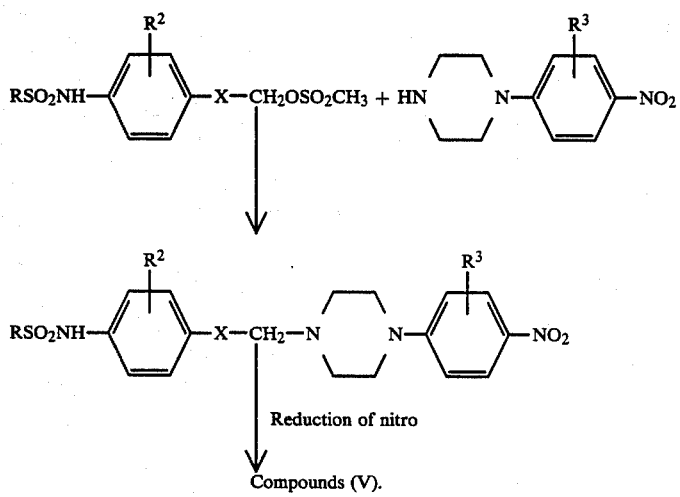

An analogous sequence can be carried out to obtain the compounds (VI).

(5) Preparation of compounds in which X is —CH(OH)— is most conveniently carried out by the reduction of the corresponding carbonyl compounds (X=CO) in a conventional manner, e.g. using an anionic hydride derivative of boron or aluminium. The preferred reducing agent is sodium borohydride, the reaction typically being carried out in a reaction-inert organic solvent, e.g. ethanol or methanol optionally with dimethylformamide or water as co-solvent at temperatures of between room temperature and, say, 100° C. It is usually most convenient to carry out the reaction under reflux. The compounds in which X is —CO— can also be reduced to compounds in which X is —$CH_2$— by the use of an appropriate reducing agent such as Zn/HCl.

The following Examples, in which all temperatures are in °C., illustrate the invention:

EXAMPLE 1

(A) 1-(4-Nitrophenyl)-4-(4-nitrophenethyl)piperazine

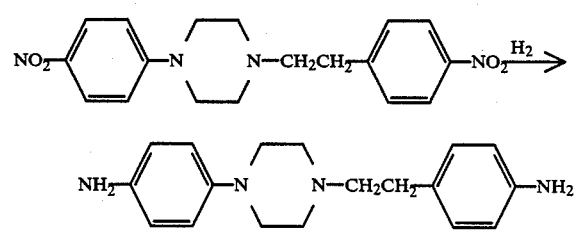

1-(4-Nitrophenyl)piperazine (4.14 g), 4-nitrophenethyl bromide (4.6 g) and sodium bicarbonate (3.4 g) in acetonitrile (75 ml) were stirred under reflux for 1 day, and then evaporated to dryness. The residue was then triturated with water (300 ml), filtered, washed with water (300 ml), and the resulting solid was crystallized from ethyl acetate, yielding the title compound, (3.62 g), m.p. 143°–5°.

N.M.R. ($CDCl_3$) δ=2.4–2.8 (m, 6H); 2.96 (m, 2H); 3.46 (t, 4H); 6.84 (d, 2H); 7.40 (d, 2H); 8.16 (d, 2H); 8.18 (d, 2H) ppm.

Analysis %: Found: C, 60.6; H, 5.6; N, 15.8; Calculated for $C_{18}H_{20}N_4O_4$: C, 60.7; H, 5.7; N, 15.7.

(B) 1-(4-Aminophenyl)-4-(4-aminophenethyl)piperazine 1-(4-Nitrophenyl)-4-(4-nitrophenethyl)piperazine (3.35 g) in methylated spirit (400 ml) was hydrogenated at 45° and 60 psi over 10% Pd/C (about 300 mg) for 3 hours. The catalyst was then removed by filtration and the filtrate evaporated to dryness, giving an off-white residual solid which was crystallized from ethyl acetate (charcoal); yield of the title compound 2.1 g, m.p. 156°–8°.

N.M.R. (CDCl$_3$) δ=2.55–2.8 (m, 8H); 3.10 (m, 4H); 3.3–3.65 (m, 4H); 6.6–6.7 (m, 4H); 6.85 (d, 2H); 7.02 (d, 2H) ppm.

Analysis %: Found: C, 72.9; H, 8.2; N, 18.9; Calculated for C$_{18}$H$_{24}$N$_4$: C, 72.8; H, 8.3; N, 18.8.

(C)
1-(4-Methanesulphonamidophenyl)-4-(4-methanesulphonamidophenethyl)piperazine

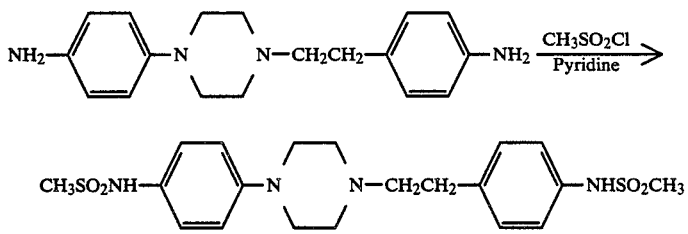

1-(4-Aminophenyl)-4-(4-aminophenethyl)piperazine (1.9 g) was dissolved in dry pyridine (15 ml) and methanesulphonyl chloride (1.85 g) was added dropwise with stirring. The mixture was stirred overnight, evaporated to dryness, and the residue triturated with aqueous sodium bicarbonate. The insoluble product was washed with water and digested with ethyl acetate/methanol then cooled and filtered, giving the pure title compound (2.1 g) as a white solid, m.p. 254°–6° (dec.).

N.M.R. (CD$_3$SOCD$_3$) δ=2.33 (m, 6H); 2.70 (m, 2H); 2.84 (s, 3H); 2.94 (s, 3H); 6.88 (d, 2H); 7.08 (d, 2H); 7.11 (d, 2H); 7.19 (d, 2H); 9.40 (bs, 2H) ppm.

Analysis %: Found: C, 52.9; H, 6.2; N, 12.3; Calculated for C$_{20}$H$_{28}$N$_4$O$_4$S$_2$: C, 53.1; H, 6.2; N, 12.4.

EXAMPLE 2
(A) 1-(2-Chloro-4-nitrophenyl)piperazine

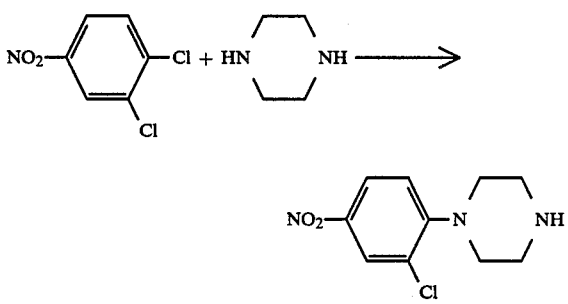

3,4-Dichloronitrobenzene (10 g), piperazine (30 g) and dioxan (10 ml) were stirred for 4 hours under gentle reflux (internal temp. 120°–130°). The mixture was then cooled and water (50 ml) was added; the desired product crystallized out and was filtered off, washed with water and dried: yield of the compound 11.32 g. A small portion (0.6 g) was recrystallized from petroleum b.p. 60°–80°/ethyl acetate, yielding the product, (0.36 g), m.p. 100°–102°.

N.M.R. (CDCl$_3$) δ=2.9–3.3 (m, 8H); 6.98 (d, 1H); 7.91 (d, ½H); 8.02–8.18 (m, 1½H) ppm.

Analysis %: Found: C, 49.6; H, 5.0; N, 17.2; Calculated for C$_{10}$H$_{12}$ClN$_3$O$_2$: C, 49.7; H, 5.0; N, 17.4.

(B)
1-(2-Chloro-4-nitrophenyl)-4-(4-nitrophenethyl)piperazine

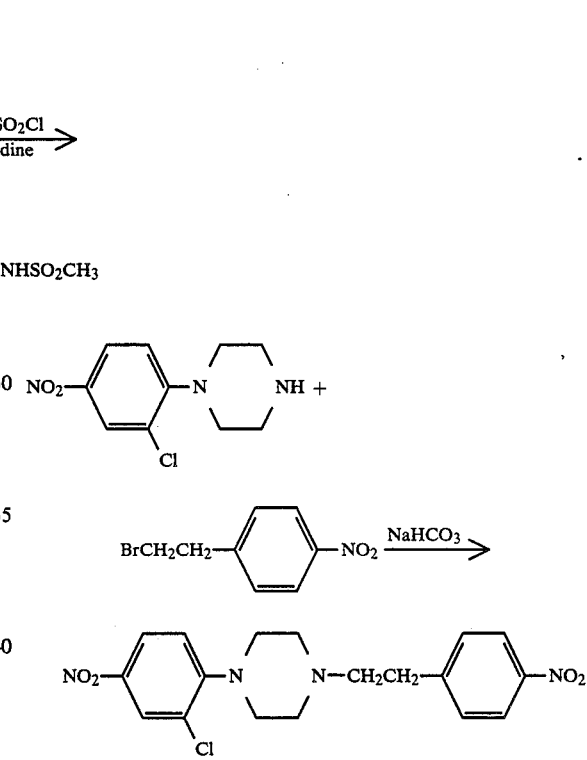

The title compound, m.p. 102°–4°, was prepared similarly to the procedure of Example 1(A) from 1-(2-chloro-4-nitrophenyl)piperazine (1.2 g), 4-nitrophenethyl bromide (1.15 g) and sodium bicarbonate (0.85 g). The yield of the title compound was 0.37 g (from ethyl acetate), m.p. 100°–102°. A second batch had an m.p. of 102°–4° (from ethyl acetate/methanol)

N.M.R. (CDCl$_3$) δ=2.73 (m, 6H); 2.96 (m, 2H); 3.26 (m, 4H); 7.06 (d, 1H); 7.40 (d, 2H); 8.09–8.18 (m, 3H); 8.26 (d, 1H) ppm.

Analysis %: Found: C, 55.4; H, 4.8; N, 14.4; Calculated for C$_{18}$H$_{19}$ClN$_4$O$_4$: C, 55.3; H, 4.9; N, 14.3.

(C)
1-(4-Amino-2-chlorophenyl)-4-(4-aminophenethyl)piperazine

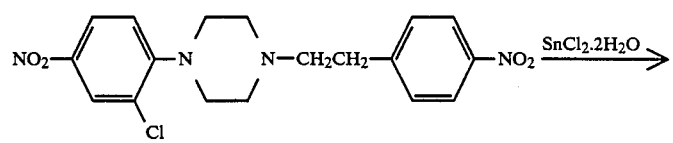

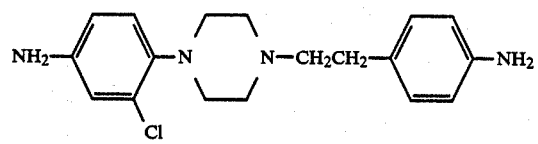

1-(2-Chloro-4-nitrophenyl)-4-(4-nitrophenethyl)piperazine (1.0 g), stannous chloride dihydrate (5.7 g) and ethanol (50 ml) were stirred under reflux for 1.25 hours, the mixture was evaporated to low bulk, and added to aqueous 5% sodium hydroxide (100 ml). The mixture was then extracted three times with dichloromethane and the combined organic extracts were dried (sodium sulphate) and evaporated to yield a yellow oil which solidified: yield of the title compound 0.6 g, m.p. 109°–112°. It was used in the next stage without further purification.

N.M.R. (CDCl$_3$) δ=2.6–2.8 (m, 8H); 3.03 (bs, 4H); 3.55 (s, 2H); 3.59 (s, 2H); 6.58 (m, 1H); 6.66 (d, 2H); 6.76 (d, 1H); 6.94 (d, 1H); 7.04 (d, 2H) ppm.

Analysis %: Found: C, 64.6; H, 7.0; N, 16.6; Calculated for C$_{18}$H$_{23}$ClN$_4$: C, 65.3; H, 7.0; N, 16.9.

(D) 1-(2-Chloro-4-methanesulphonamidophenyl)-4-(4-methanesulphonamidophenethyl)piperazine

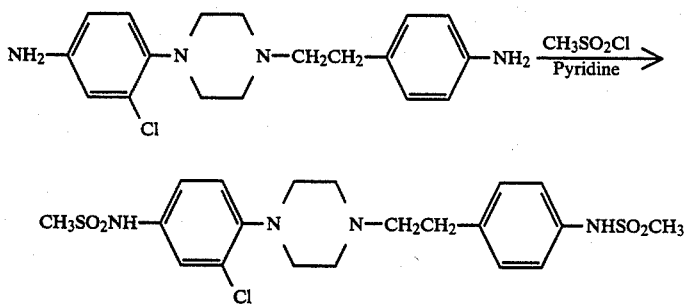

The title compound (0.52 g), was prepared similarly to the procedure of Example 1(C) from methanesulphonyl chloride (0.44 g), 1-(4-amino-2-chlorophenyl)-4-(4-aminophenethyl)piperazine (0.55 g), and pyridine (10 ml).

The m.p. of the product was 212°–215° (from methanol/ethyl acetate).

N.M.R. (CD$_3$SOCD$_3$) δ=2.55–2.58 (m, 4H); 2.72 (m, 2H); 2.94 (m, 8H); 3.33 (s, 4H); 7.10–7.23 (m, 7H); 9.63 (bs, 2H) ppm.

Analysis %: Found: C, 49.4; H, 5.6; N, 11.1; Calculated for C$_{20}$H$_{27}$ClN$_4$O$_4$S: C, 49.3; H, 5.6; N, 11.5.

EXAMPLE 3

(A) 1-Acetyl-4-(3-fluoro-4-nitrophenyl)piperazine

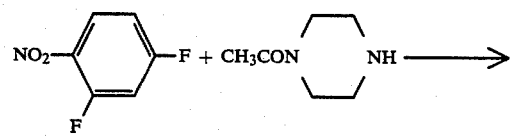

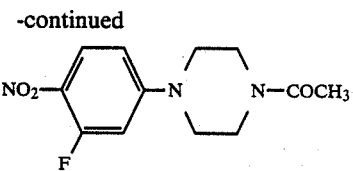

2,4-Difluoronitrobenzene (4.29 g) and 1-acetylpiperazine (8.05 g) were dissolved in methanol (10 ml), kept overnight (17 hours) at ambient temperature, then diluted with methylene chloride (10 ml). The solution was washed with water (2×10 ml) and the methylene chloride layer was washed with water (2×40 ml) and evaporated to give a viscous orange oil (7.76 g) which slowly solidified. This product was dissolved in methanol (5 ml) and ether (15 ml) was added, precipitating a yellow solid (0.20 g) which was discarded. The filtrate was evaporated to yield a viscous oil (7.3 g) which was dissolved in 25 ml 20% methanol in ether, and chromatographed, under slight pressure, on Merck 60H (Trade Mark) t.l.c. grade silica, developing and eluting with the same solvent, collecting first the undesired isomer 1-acetyl-4-(5-fluoro-2-nitrophenyl)piperazine (4.73 g) from 120 to 250 ml eluate, identified by a lowest HF coupling of 5.8 Hz in the $^{19}$F N.M.R., consistent only with absence of hydrogen para to fluorine, followed by the desired 1-acetyl-4-(3-fluoro-4-nitrophenyl)piperazine (1.61 g), a yellow solid from 280 to 630 ml eluate, identified by a para HF coupling of −1.0 Hz in the $^{19}$F N.M.R.

N.M.R. (CDCl$_3$) δ=2.18 (s, 3H); 3.48 (m, 4H); 3.69 (m, 2H); 3.82 (t, 2H); 6.53–6.64 (m, 2H); 8.08 (t, 1H) ppm.

The product was used directly in the next stage.

(B) 1-(3-Fluoro-4-nitrophenyl)piperazine hydrochloride

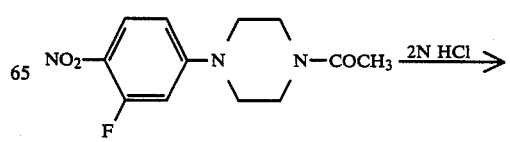

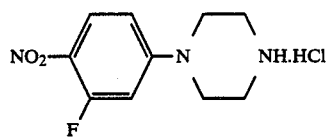

1-Acetyl-4-(3-fluoro-4-nitrophenyl)piperazine (1.08 g), and 2N hydrochloric acid (20 ml) were refluxed for 30 minutes. The solution was then evaporated to dryness, the residue triturated with methanol, the whole re-evaporated to remove hydrochloric acid, and the residue crystallized from methanol/ethanol, yielding the title compound, (0.78 g), m.p. 271°-3°.

N.M.R. (CD$_3$SOCD$_3$) δ=3.18 (t, 4H); 3.65 (t, 4H); 6.92 (d, 1H); 7.04 (d, 1H); 8.03 (dd, 1H); 9.68 (bs, 2H) ppm.

Analysis %: Found: C, 45.9; H, 4.9; N, 16.2; Calculated for C$_{10}$H$_{12}$FN$_3$O$_2$.HCl: C, 45.9; H, 5.1; N, 16.1.

(C)
1-(3-Fluoro-4-nitrophenyl)-4-(4-nitrophenethyl)-piperazne

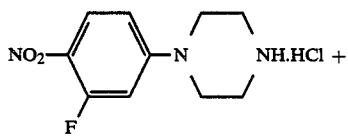

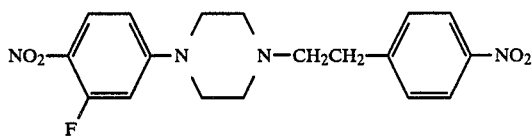

1-(3-Fluoro-4-nitrophenyl)piperazine hydrochloride (0.50 g), 4-nitrophenethyl bromide (0.44 g), sodium iodide (0.29 g) and potassium carbonate (0.27 g) in acetonitrile (11 ml) were refluxed for 2.75 hours. The mixture was then evaporated to dryness, partitioned between 5% methanol in dichloromethane and water, and the organic fraction chromatographed over silica, developing and eluting with 5% methanol in dichloromethane to yield the pure product as a yellow solid (0.19 g), R$_f$ 0.57 (5% MeOH/CH$_2$Cl$_2$ on silica). The product was used directly in the next stage.

(D)
1-(3-Fluoro-4-aminophenyl)-4-(4-aminophenethyl)piperazine

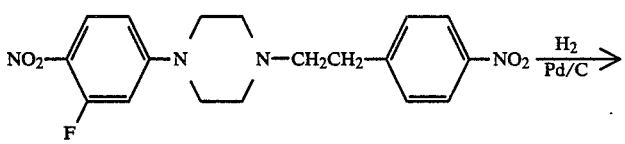

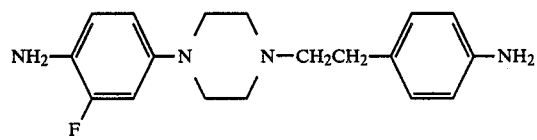

1-(3-Fluoro-4-nitrophenyl)-4-(4-nitrophenethyl)piperazine (0.19 g) and 10% palladium on carbon (150 mg) were hydrogenated at 4 atmospheres and 60° until completion of hydrogen uptake. The catalyst was then filtered off, the solvent evaporated, and the residual product (0.06 g) used directly in the next stage.

N.M.R. (CDCl$_3$) δ=2.55-2.82 (bm, 6H); 2.94-3.24 (bm, 6H); 3.63 (bs, 4H); 6.40-7.06 (complex, 7H) ppm.

(E)
1-(3-Fluoro-4-methanesulphonamidophenyl)-4-(4-methanesulphonamidophenethyl)piperazine

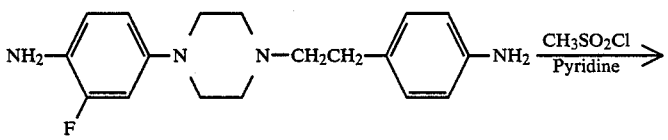

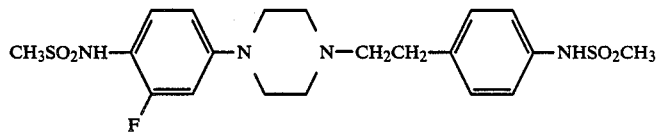

1-(3-Fluoro-4-aminophenyl)-4-(4-aminophenethyl)-piperazine (0.06 g) was dissolved in pyridine (4.5 ml) and methanesulphonyl chloride (0.13 g) was added. The mixture was stirred at room temperature overnight, the pyridine removed by evaporation, and the residue chromatographed over silica, developing and eluting with 10% methanol in dichloromethane. The fractions containing the product were evaporated to give a residue (0.30 g) which was crystallized from methanol, yielding the pure title compound, (0.016 g), m.p. 232°–4°.

N.M.R. (CDCl$_3$): δ=2.54 (m, 6H); 2.72 (m, 2H); 2.89 (s, 3H); 2.94 (s, 3H); 3.14 (m, 4H); 6.70–6.85 (m, 2H) 7.08+7.12 (3H); 7.18+7.22 (2H); 9.35 (vbs, 2H) ppm.

Analysis %: Found: C, 51.1; H, 5.9; N, 11.9; Calculated for C$_{20}$H$_{27}$FN$_4$O$_4$S$_2$: C, 51.0; H, 5.8; N, 11.9.

EXAMPLE 4

(A) 1-Acetyl-4-(3-methyl-4-nitrophenyl)piperazine

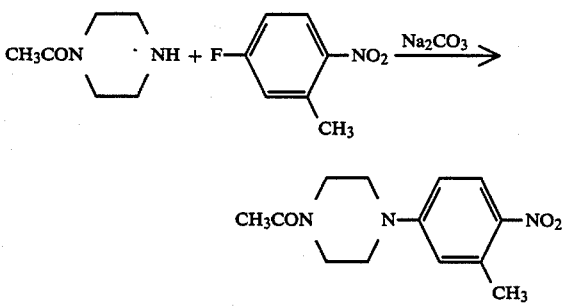

1-Acetylpiperazine (6.23 g), 5-fluoro-2-nitrotoluene (7.51 g) and sodium carbonate (5.12 g) in dimethylformamide (40 ml) were stirred at 100° overnight, evaporated, and the residue partitioned between ethyl acetate and water. The organic layer was dried (sodium sulphate), evaporated, and the residue chromatographed over Merck (Trade Mark) t.l.c. grade silica, developing and eluting with 5% methanol in dichloromethane, yield 10.92 g of the title compound. A small portion was recrystallized from methanol/ethyl acetate, m.p. 133°–7°.

N.M.R. (CDCl$_3$) δ=2.18 (s, 3H); 2.64 (s, 3H); 3.43 (m, 4H); 3.66 (m, 2H); 3.81 (m, 2H); 6.69 (m, 2H), 8.11 (d, 1H) ppm.

Analysis %: Found: C, 58.9; H, 6.6; N, 16.2; Calculated for C$_{13}$H$_{17}$N$_3$O$_3$: C, 59.3; H, 6.5; N, 16.0.

(B) 1-Acetyl-4-(4-amino-3-methylphenyl)piperazine

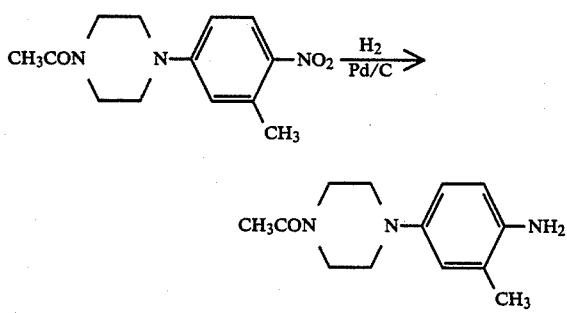

1-Acetyl-4-(3-methyl-4-nitrophenyl)piperazine (0.5 g) and 5% palladium on carbon (0.1 g) in ethanol (20 ml) were hydrogenated at 60° and 60 p.s.i for 2 hours after which the catalyst was filtered off and the filtrate evaporated. The residue was partitioned between dichloromethane and water, and the aqueous layer extracted two more times with dichloromethane. The combined organic layers yielded 0.42 g of residue (of the title compound) on evaporation. This was recrystallized, m.p. 126°–9° (methanol/ethyl acetate).

N.M.R. (CDCl$_3$) δ=2.14 (s, 3H); 2.17 (s, 3H); 3.01 (m, 4H); 3.43 (bs, 2H); 4.60 (m, 2H); 4.87 (m, 2H).

Analysis %: Found: C, 66.7; H, 8.2; N, 17.9; Calculated for C$_{13}$H$_{19}$N$_3$O: C, 66.9; H, 8.2; N, 18.0.

(C) 1-Acetyl-4-(4-methanesulphonamido-3-methylphenyl)-piperazine

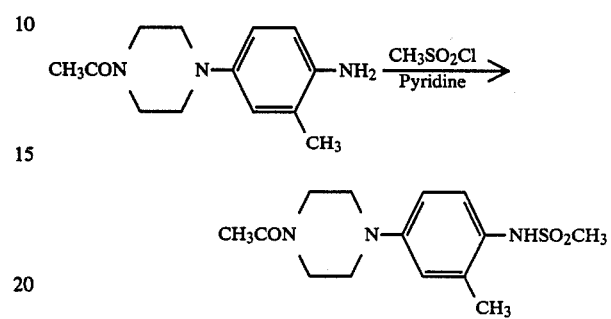

1-Acetyl-4-(4-amino-3-methylphenyl)piperazine (7.89 g) was dissolved in pyridine (130 ml). Methanesulphonyl chloride (7.9 ml) was added dropwise with stirring. The mixture was reduced in volume after 2 hours by evaporation and then stirred overnight. The resulting slurry was partitioned between water (125 ml) and dichloromethane (100 ml), and the aqueous layer was further extracted with dichloromethane (2×100 ml), 5% methanol in dichloromethane (2×100 ml), and ethyl acetate (2×125 ml). The combined organic layers were dried (sodium sulphate) and evaporated, and the residue was chromatographed in 5% methanol in dichloromethane over t.l.c. grade silica, the product-containing fractions, after evaporation, yielding a foam (5.93 g), Rf 0.29 (5% methanol/dichloromethane/silica), used directly in step (D). A small sample from a second run was recrystallized from ethyl acetate/hexane, m.p. 153°–4°.

N.M.R. (CDCl$_3$) δ=2.14 (s, 3H); 2.34 (s, 3H); 2.97 (s, 3H); 3.17 (m, 4H); 3.61 (t, 2H); 3.76 (t, 2H); 6.12 (s, 1H); 6.76 (m, 2H); 7.28 (m, 1H) ppm.

Analysis %: Found: C, 54.0; H, 6.8; N, 13.4; Calculated for C$_{14}$H$_{21}$N$_3$O$_3$S: C, 54.0; H, 6.8; N, 13.5.

(D) 1-(4-Methanesulphonamido-3-methylphenyl)piperazine ¼ hydrate

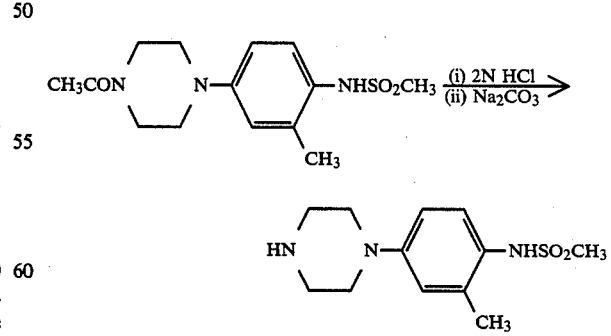

1-Acetyl-4-(4-methanesulphonamido-3-methylphenyl)piperazine (5.93 g) and 2N aqueous hydrochloric acid (85 ml) were refluxed for 2 hours, cooled, evaporated to low bulk, basified with sodium carbonate to pH 9–10 and extracted with 5×100 ml 5% methanol in dichloromethane. The organic layers were combined and evaporated to give the title compound as a brown foam, (4.78 g), m.p. 79°–81°.

N.M.R. (CDCl$_3$) δ=2.13 (s, 3H); 2.96 (s, 3H); 3.05 (m, 4H); 3.15 (m, 4H); 6.76 (m, 2H); 7.16 (m, 1H).

Analysis %: Found: C, 52.6; H, 6.8; N, 15.2; Calculated for C$_{12}$H$_{19}$N$_3$O$_2$S.¼H$_2$O: C, 52.6; H, 7.2; N, 15.3.

(E) 4-Methanesulphonamidophenethyl methanesulphonate

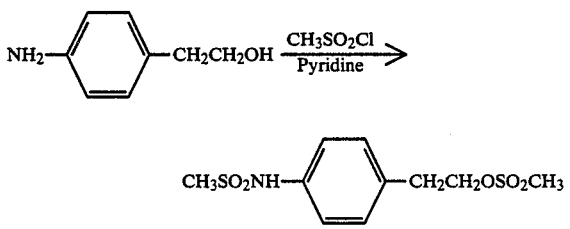

4-Aminophenethyl alcohol (2.74 g) was dissolved in dichloromethane (10 ml) and pyridine (5 ml) and then methanesulphonyl chloride (2×2.52 g) was added in 2 portions one hour apart, with stirring at 0°. After a further 2 hours, the mixture was acidified (to pH about 2) with 2N aqueous hydrochloric acid. The title compound (4.85 g) was filtered from the two-phase mixture. The organic layer plus a further dichloromethane extract of the aqueous layer yielded a further 0.95 g product after drying (sodium sulphate) and evaporation. The combined solids were washed with ether and recrystallized from ethyl acetate, yield of the title compound 4.13 g, m.p. 135°–7°.

N.M.R. [(CD$_3$)$_2$CO] δ=3.07 (s, 3H); 3.10 (s, 3H); 3.15 (t, 2H); 4.52 (t, 2H); 7.36 (s, 4H); 8.47 (bs, 1H) ppm.

Analysis %: Found: C, 40.6; H, 5.2; N, 4.9; Calculated for C$_{10}$H$_{15}$NO$_5$S$_2$: C, 40.9; H, 5.2; N, 4.8.

(F) 1-(4-Methanesulphonamido-3-methylphenyl)-4-(4-methanesulphonamidophenethyl)piperazine

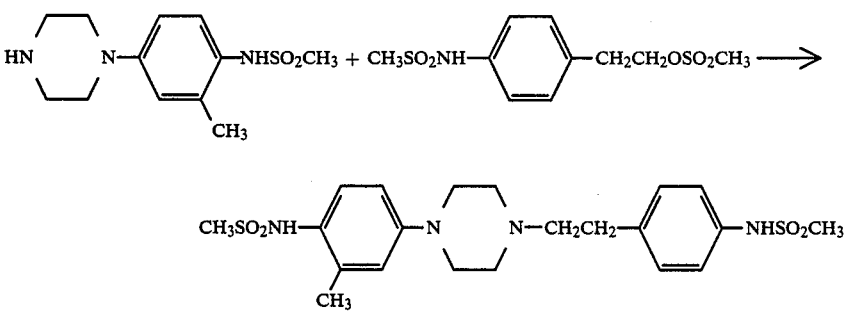

4-Methanesulphonamidophenethyl methanesulphonate (1.47 g) and 1-(4-methanesulphonamido-3-methylphenyl)piperazine ¼ hydrate (1.37 g) in ethanol (15 ml) were refluxed overnight, evaporated to dryness, and partitioned between ethyl acetate and water. The title compound (0.2 g) was filtered from the 2-phase mixture and recrystallised from methanol/acetone, yield 0.128 g, m.p. 235°–7°.

N.M.R. (CD$_3$SOCD$_3$) δ=2.23 (s, 3H); 2.54 (m, 6H); 2.72 (t, 2H); 2.87 (s, 3H); 2.94 (s, 3H); 3.11 (m, 4H); 6.70–6.84 (m, 2H); 7.03–7.12 (s, 3H); 7.13–7.21 (d, 2H); 9.13 (bs, 2H) ppm.

Analysis %: Found: C, 54.3; H, 6.4; N, 12.0; Calculated for C$_{21}$H$_{30}$N$_4$O$_4$S$_2$: C, 54.0; H, 6.5; N, 12.0.

EXAMPLE 5

(A) 1-Actyl-4-(4-aminophenyl)piperazine

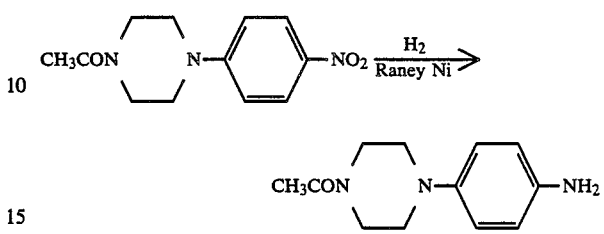

1-Acetyl-4-(4-nitrophenyl)piperazine [Ger. Pat. No. 1,239,940; Chem. Abs., 67, 101031z (1967)] (76.64 g) in ethanol (1000 ml) was hydrogenated over Raney nickel at 40° and 60 p.s.i. for 4 hours. The catalyst was then filtered off and the filtrate evaporated to give a residual solid which was crystallised from ethyl acetate, yield of the title compound 47.88 g, m.p. 129°–130°.

N.M.R. (CDCl$_3$) δ=2.12 (s, 3H); 2.90–3.09 (t, 4H); 3.50–3.8 (m, 4H); 6.52, 6.67, 6.72, 6.88 (ABq, 4H) ppm.

Analysis %: Found: C, 65.8; H, 7.8; N, 19.5; Calculated for C$_{12}$H$_{17}$N$_3$O: C, 65.7; H, 7.8; N, 19.2.

(B) 1-Acetyl-4-(4-methanesulphonamidophenyl)piperazine

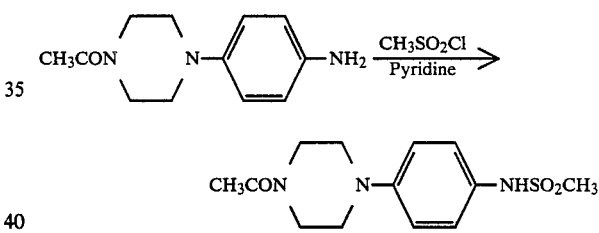

To 1-Acetyl-4-(4-aminophenyl)piperazine (10.96 g) in ice-cold pyridine (100 ml) was added methanesulphonyl chloride (6.3 g) dropwise. The mixture was then stirred at ambient temperature overnight and the pyridine removed in vacuo. The residue was triturated with aqueous sodium bicarbonate, and the resulting solid was washed (water) and crystallized from methanol/ethyl acetate (charcoal). The yield of the title compound was 9.97 g, m.p. 165°–7°.

N.M.R. (CDCl$_3$) δ=2.17 (s, 3H); 2.97 (s, 3H); 3.16 (m, 4H); 3.63 (t, 2H); 3.77 (t, 3H); 6.67 (s, 1H); 6.91 (d, 2H); 7.20 (d, 2H) ppm.

Analysis %: Found: C, 52.4; H, 6.3; N, 14.1; Calculated for $C_{13}H_{19}N_3O_3S$: C, 52.5; H, 6.4; N, 14.1.

(C) 1-(4-Methanesulphonamidophenyl)piperazine hydrochloride

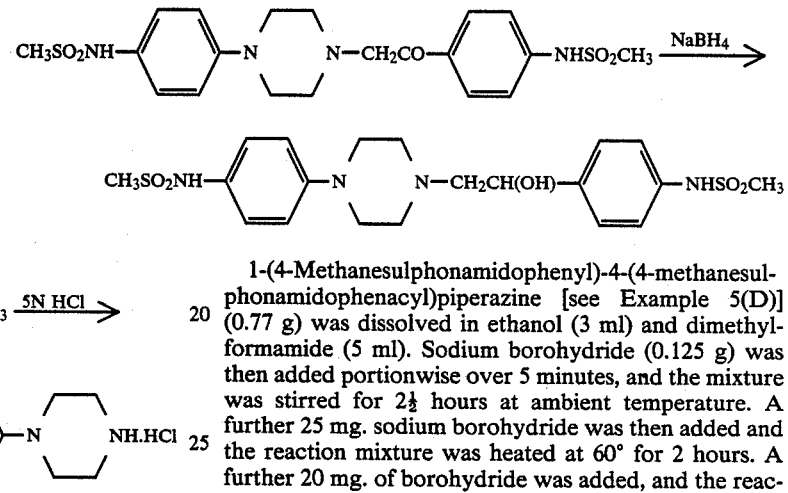

1-Acetyl-4-(4-methanesulphonamidophenyl)piperazine (9.6 g) and 5N aqueous hydrochloric acid (100 ml) were heated at 100° for 1 hour, the solvent was evaporated, and the residue dried by azeotroping with toluene. The residue was crystallised from ethanol, yield of the title compound 8.26 g, m.p. 230° (dec.).

N.M.R. $(CD_3SOCD_3)$ δ=2.85 (s, 3H); 3.15 (s, 4H); 3.30 (m, 4H); 6.95 (d, 2H); 7.10 (d, 2H); 9.27 (bs, 2H); 9.37 (s, 1H) ppm.

Analysis %: Found: C, 44.5; H, 6.3; N, 14.0; Calculated for $C_{11}H_{17}N_3O_2S.HCl$: C, 45.3; H, 6.2; N, 14.4.

(D)
1-(4-Methanesulphonamidophenyl)-4-(4-methanesulphonamidophenacyl)piperazine

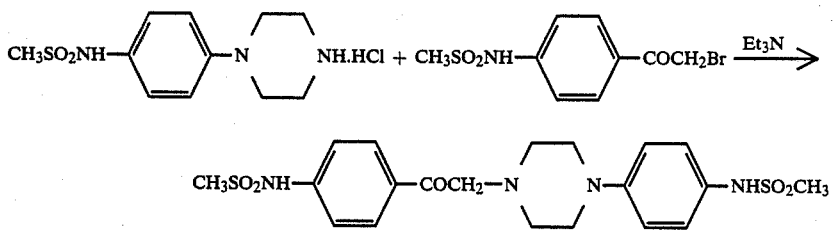

1-(4-Methanesulphonamidophenyl)piperazine hydrochloride (1.18 g), 4-methanesulphonamidophenacyl bromide (1.16 g), [see *J. Med. Chem*, 9, 88 (1966)], triethylamine (0.82 g), methanol (10 ml) and dichloromethane (10 ml) were warmed briefly to attain homogeneity, then stirred at ambient temperature for 4 hours, evaporated to dryness, the residue triturated and washed with water, and then crystallized from methanol/acetone. The yield of the title compound was 0.88 g, m.p. 222°–5° (dec.).

N.M.R. $(CD_3SOCD_3)$ δ=2.62 (bs, 4H); 3.10 (bs, 8H); 3.34 [s, 2H (+$H_2O$)]; 3.82 (s, 2H); 6.88 (d, 2H); 7.07 (d, 2H); 7.27 (d, 2H); 7.98 (d, 2H); 9.22 (s, 1H); 10.31 (bs, 1H) ppm.

Analysis %: Found: C, 51.2; H, 5.2; N, 11.7; Calculated for $C_{20}H_{26}N_4O_5S_2$: C, 51.5; H, 5.6; N, 12.0.

EXAMPLE 6

1-(4-Methanesulphonamidophenyl)-4-[2-hydroxy-2-(4-methanesulphonamidophenyl)ethyl]piperazine 1-(4-Methanesulphonamidophenyl)-4-(4-methanesulphonamidophenacyl)piperazine [see Example 5(D)] (0.77 g) was dissolved in ethanol (3 ml) and dimethylformamide (5 ml). Sodium borohydride (0.125 g) was then added portionwise over 5 minutes, and the mixture was stirred for 2½ hours at ambient temperature. A further 25 mg. sodium borohydride was then added and the reaction mixture was heated at 60° for 2 hours. A further 20 mg. of borohydride was added, and the reaction mixture was heated at 70° for 4½ hours. The mixture was then diluted with water, precipitating the impure product containing some unreduced starting material (0.51 g after drying). This impure product was refluxed for 4½ hours in ethanol (35 ml), adding sodium borohydride (110 mg) portionwise during the first 2 hours. The mixture was then evaporated, the residue washed with water, and crystallized from methanol, yield of the pure title compound 0.118 g., m.p. 230°-2° (dec.).

N.M.R. $(CD_3SOCD_3)$ δ=2.37–2.56 (m, 2H); 2.62 (m, 4H); 2.85 (s, 3H); 2.94 (s, 3H); 4.72 (m, 1H); 5.02 (d, 1H); 6.90 (d, 2H); 7.06 (d, 2H); 7.14 (d, 2H); 7.32 (d, 2H); 9.1–9.8 (bs, 2H) ppm.

Analysis %: Found C, 50.9; H, 6.1; N, 11.9; Calculated for $C_{20}H_{28}N_4O_5S_2$: C, 51.3; H, 6.0; N, 12.0.

EXAMPLE 7

1-(4-Methanesulphonamidophenyl)-4-(4-methanesulphonamidophenethyl)piperazine hydrochloride hemihydrate 1-(4-Methanesulphonamidophenyl)-4-(4-methanesulphonamidophenethyl)piperazine [1.61 g.—see Example 1(C)] was dissolved in 2N aqueous hydrochloric acid (3.9 ml) and the reaction mixture was evaporated to dryness, giving a solid containing a trace of a reddish impurity. This solid was dissolved in methanol (250 ml) and boiled with charcoal (0.5 g), filtered, and the filtrate evaporated to about 65 ml, re-charcoaled (1.5 g. charcoal), and re-filtered. The filtrate was evaporated to about 20 ml, filtered, and ether (20 ml) was added. The solution was then evaporated to about 20 ml and more ether (10 ml) was added. the solution was left to cool, the resulting crystals were filtered off, washed with ether/methanol (40 ml 1:1 then 30 ml 2:1), then with ether (30 ml) and finally dried in vacuo. The yield of the pure title salt, m.p. (dec.) 254°-6°, was 1.37 g.

Analysis %: Found: C, 48.43; H, 5.86; N, 11.09; Calculated for $C_{20}H_{28}N_4S_2 \cdot HCl \cdot \frac{1}{2}H_2O$: C, 48.22; H, 6.07; H, 11.25.

We claim:

1. A process for the prevention or reduction of cardiac arrhythmias in a human being which comprises administering to said human being a cardiac arrhythmia preventing or reducing amount of a compound of the formula (I):

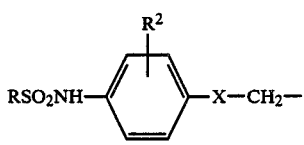
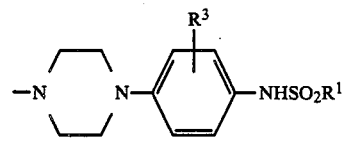
(I)

or a pharmaceutically acceptable salt thereof, wherein R and $R^1$, which are the same or different, are $C_1$-$C_4$ alkyl;

$R^2$ and $R^3$, which are the same or different, are H, halo or $C_1$-$C_4$ alkyl; and X is —$CH_2$—,

or —CH(OH)—.

2. A process according to claim 1 wherein R and $R^1$ are each $CH_3$; $R^2$ is H; and $R^3$ is H, $CH_3$, Cl or F.

3. A process according to claim 2 wherein X is —$CH_2$—.

4. The process according to claim 3 wherein R and $R^1$ are each $CH_3$; each of $R^2$ and $R^3$ is hydrogen; and X is —$CH_2$—, said compound having the formula:

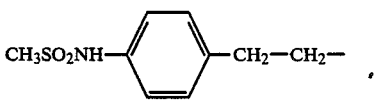
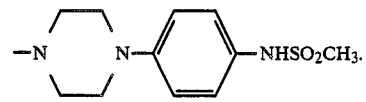

* * * * *

UNITED STATES PATENT AND TRADEMARK OFFICE
CERTIFICATE OF CORRECTION

PATENT NO. : 4,797,401

DATED : January 10, 1989

INVENTOR(S) : John E. G. Kemp and Peter E. Cross

It is certified that error appears in the above-identified patent and that said Letters Patent is hereby corrected as shown below:

Column 7, line 25 and 45-52, formula (IV) at lines 45-52 should appear at line 25.

Column 13, line 57, "$C_{20}H_{27}ClN_4O_4S$" should read -- $C_{20}H_{27}ClN_4O_4S_2$ -- .

Signed and Sealed this

Twenty-seventh Day of June, 1989

Attest:

DONALD J. QUIGG

Attesting Officer

Commissioner of Patents and Trademarks